United States Patent [19]

Ross et al.

[11] Patent Number: 4,475,949

[45] Date of Patent: Oct. 9, 1984

[54] ALKALI EARTH METAL OXIDE-BASED COATING COMPOSITIONS

[75] Inventors: Norman C. Ross, Allison Park; Jeffrey J. Lettrich, Tarentum, both of Pa.

[73] Assignee: Kimes Corporation, Allison Park, Pa.

[21] Appl. No.: 440,521

[22] Filed: Nov. 10, 1982

[51] Int. Cl.$^3$ .............................................. C09D 5/08
[52] U.S. Cl. ........................... 106/14.35; 106/14.13; 106/14.28; 106/14.29; 106/14.36; 106/14.38; 106/270; 252/33; 252/39; 252/389 R; 252/395; 252/396
[58] Field of Search ...................... 252/33, 39, 389.61, 252/395, 396; 106/14.13, 14.28, 14.29, 14.35, 14.36, 14.38, 270

[56] References Cited

U.S. PATENT DOCUMENTS

| | | | |
|---|---|---|---|
| 3,057,896 | 10/1962 | Schlicht et al. | 252/33 |
| 3,242,079 | 3/1966 | McMillen | 252/33 |
| 3,372,115 | 3/1968 | McMillen | 252/33 |
| 3,865,737 | 2/1975 | Kemp | 252/33 |
| 4,094,801 | 6/1978 | Forsberg | 252/33 |

FOREIGN PATENT DOCUMENTS 1570909  7/1980  United Kingdom .

*Primary Examiner*—Lorenzo B. Hayes
*Attorney, Agent, or Firm*—Webb, Burden, Robinson & Webb

[57] ABSTRACT

A noncarbonated complex for use in preparing coating compositions is comprised of the reaction product of a basic oxide selected from the group consisting of calcium and magnesium oxide and mixtures thereof; an organic sulfonic acid having an equivalent weight of about 300 to 750 grams per equivalent; and water. The molar ratio of basic oxide to organic sulfonic acid is at least 10:1. The molar ratio of water to basic oxide is less than 2.5:1 and greater than 0.5:1 when the basic oxide is at least 30 percent calcium oxide. The molar ratio of water to basic oxide is less than 0.7:1 and greater than 0.3:1 when the basic oxide is less than 30 percent calcium oxide.

12 Claims, No Drawings

ALKALI EARTH METAL OXIDE-BASED COATING COMPOSITIONS

BACKGROUND OF THE INVENTION

1. Field of the Invention

This invention relates to coating compositions based upon noncarbonated complexes of calcium and magnesium oxide.

2. Description of the Prior Art

Compositions based upon high stoichiometric excesses of magnesium carbonates including alkylbenzene sulfonic acids are well known. Illustrative of such compositions are those disclosed in U.S. Pat. Nos. 3,242,079; 3,372,115; 3,865,737 and British Pat. No. 1,570,909. Additionally, noncarbonated magnesium-containing complexes for coating compositions and oil additives are disclosed in U.S. Pat. No. 4,094,801.

The compounds taught in U.S. Pat. No. 4,094,801 are based upon specific molar ratios of magnesium oxide, oleophilic acids including sulfonic acids, and water. More particularly, these compositions are combined with other hydrophobic compounds such as waxes, along with polymeric materials and the like and deemed useful as anticorrosion compositions. This U.S. patent teaches that it is necessary to have a molar ratio of about 0.7:1 to 3:1 water to magnesium oxide, and in the preparation of coating compositions, molar ratios of 1:1 and 3:1 are most desirable.

In accordance with the present invention, compositions containing predominantly magnesium oxide can be prepared which have excellent salt spray resistance, rendering them particularly useful for anticorrosion coating compositions. Additionally, in accordance with the present invention, coating compositions have been prepared utilizing oxides other than magnesium oxide, which have excellent anticorrosion properties.

BRIEF DESCRIPTION OF THE INVENTION

A noncarbonated complex for use in preparing coating compositions is comprised of the reaction product of a basic oxide selected from the group consisting of calcium and magnesium oxide and mixtures thereof; and organic sulfonic acids having equivalent weights of about 300 to 750 grams per equivalent; and water. The molar ratio of basic oxide to organic sulfonic acid is at least 10:1. The molar ratio of water to basic oxide is less than 2.5:1 and greater than 0.5:1 when the basic oxide is at least 30 percent calcium oxide. The molar ratio of water to basic oxide is less than 0.7:1 and greater than 0.3:1 when the basic oxide is less than 30 percent calcium oxide.

DETAILED DESCRIPTION OF THE INVENTION

The magnesium oxide useful in the practice of the invention is the reactive magnesium oxide as distinguished from dead burned magnesium oxide which is used in refractory applications and the like. In addition to the reactive magnesium oxide, hydrated magnesium oxide may be used in the practice of the invention. However, the hydrated magnesium oxide should have less than 0.7 mole of water per mole of magnesium oxide. The calcium oxide useful in the practice of the invention is the reactive calcium oxide as distinguished from dead burned lime. Further, calcium hydroxide may also be used as long as the molar ratio of water to calcium oxide is less than 2.5:1.

The organic sulfonic acids useful in the practice of the invention are those represented by the formulae $R'(SO_3H)$ and $R'Ar(SO_3H)$, wherein $R'$ is an aliphatic alkyl radical having up to 50 carbon atoms, and preferably 15 to 18 carbon atoms, and Ar is an aromatic ring. The organic sulfonic acids which have $R'$ groups of greater than 30 carbon atoms and are solid at ambient temperature (i.e. about 25° C.) are useful in forming the noncarbonated basic oxide complex in that they provide hydrophobic properties to the formulated coating composition. Exemplary of the Ar groups are benzene, naphthalene and fused ring systems along with aromatic residues. Illustrative sulfonic acids useful in the practice of the invention are, but not limited to, mahogany sulfonic acids, petrolatum sulfonic acid, mono- and polywax-substituted naphthalene sulfonic acids, cetylchlorobenzene sulfonic acids, cetylphenol sulfonic acids, cetylphenol disulfide sulfonic acids, cetoxycapryl benzene sulfonic acids, dicetyl thianthrene sulfonic acids, dilauryl beta-naphthol sulfonic acids, dicapryl nitronaphthalene sulfonic acids, paraffin wax sulfonic acids, unsaturated paraffin wax sulfonic acids, hydroxy-substituted paraffin wax sulfonic acids, tetraisobutylene sulfonic acids, tetraamylene sulfonic acids, chloro-substituted paraffin wax sulfonic acids, nitroso-substituted paraffin wax acids, petroleum naphthalene sulfonic acids, cetylcyclopentyl sulfonic acids, lauryl cyclohexyl sulfonic acids, mono- and polywax-substituted cyclohexyl sulfonic acids, "dimer alkylate" sulfonic acids and the like. Most preferred are the mono- and dialkyl aromatic sulfonic acids, wherein the alkyl groups are of a molecular weight rendering the sulfonic acid's equivalent weight of 300 to 750 grams per equivalent, and the aromatic moiety is benzene.

In addition to the alkylbenzene sulfonic acids, organic carboxylic acids may be used in combination therewith at a level of up to 50 percent of the acid content of the composition. These carboxylic acids include aliphatic, cycloaliphatic and aromatic mono- and polybasic carboxylic acids free from acetylenic unsaturation, including naphthenic acids, alkyl- or alkenyl-substituted cyclopentanoic acids, alkyl- or alkenyl-substituted cyclohexanoic acids, and alkyl- or alkenyl-substituted aromatic carboxylic acids. The aliphatic acids generally contain at least 8, and preferably at least 12 carbon atoms to render them oleophilic in nature. The cycloaliphatic and aliphatic carboxylic acids can be saturated or unsaturated. Specific examples include 2-ethylhexanoic acid, linolenic acid, propylene tetramer-substituted maleic acid, behenic acid, isostearic acid, pelargonic acid, capric acid, palmitoleic acid, linoleic acid, lauric acid, oleic acid, ricinoleic acid, undecylic acid, dioctylcyclopentanecarboxylic acid, myristic acid, dilauryldecahydronaphthalenecarboxylic acid, stearyloctahydroindenecarboxylic acid, palmitic acid, acids formed by the oxidation of petroleum hydrocarbons including petrolatum, oil and wax, and commercially available mixtures of two or more carboxylic acids such as tall oil acids, rosin acids and the like. Most preferred are the oxidation products of petrolatum.

It has been found that the ratio of components is critical in preparing corrosion-resistant coating compositions. The molar ratio of basic oxide to organic sulfonic acid is at least 10:1 and up to 30:1, and most preferably 15-20:1 in order to obtain coating compositions with excellent corrosion-inhibiting properties.

The most critical component in the system is the water which should be closely controlled. When at least 30 percent calcium oxide is used as the basic oxide, the reacted water to oxide ratio should be less than 2.5:1, and more preferably less than 1:1. When the basic oxide is less than 30 percent calcium oxide, the ratio of water to oxide is less than 0.7:1 and greater than 0.3:1. Although this holds true for corrosion-inhibiting reaction products, lube oil and fuel oil additives may have higher water ratios. In the case of calcium oxide and calcium oxide-magnesium oxide mixtures, up to about 3:1 water to oxide but greater than 0.3:1 water to oxide are operable.

It is believed by the applicants, not wishing to be bound by this theory, that the low molar ratio of water to magnesium and calcium oxide renders a composition which has water covalently bound or associated as a hydrate in the reaction product. This is contrary to the reaction products in the prior art, and particularly magnesium oxide reaction products which have higher water contents, where it was believed that it was necessary to substantially fully hydrate the magnesium oxide to provide a desirable product. Because of the high water levels of the prior art compounds, the compositions take on a substantially ionic nature, making them susceptible to attack by salt, water and other corrosion-inducing constituents. Partially reacted inorganic basic oxide is indicative of a closely associated complex or half salt which has exceptional hydrolytic stability.

In preparing the reaction products in accordance with the invention, it is necessary and desirable to utilize a solvent for the system. These solvents are typically hydrocarbon solvents having boiling points above 65° C., and more preferably above 130° C. These solvents, which are diluents only, are naphtha, hexane, kerosene, mineral oil, paraffinic hydrocarbons, Stoddard solvent, benzene, toluene, xylene, and alkylbenzenes of the type present as unsulfonated residues in the alkylbenzene sulfonic acids. Polar solvents such as higher alcohols may be utilized, but are undesirable since a nonpolar final material is desirable. The higher boiling point solvents are desirable since they can be utilized in the final product as solvents for the final coating composition.

Further, materials such as paraffin waxes, which are normally solids at room temperature, may be incorporated into the system as diluents and further impart hydrophobic properties to final coating compositions, making them even less water sensitive. Such waxes are the hydrocarbon waxes which are both crystalline, microcrystalline and noncrystalline such as petrolatum, paraffin and olefin waxes and synthetic hydrocarbon waxes such as polyethylene and other polyolefins. Further, other constituents well known to those skilled in the art may be utilized in preparing the coating compositions and reaction products of the invention. Contrary to prior art compositions, such as are taught in U.S. Pat. No. 4,094,801, the high viscosity (as a thixotrope) of the final reaction product in accordance with the present invention is due to the wax rather than the magnesium oxide complex.

Two procedures may be utilized in preparing the reaction products in accordance with the invention. The first procedure is to charge the organic sulfonic acid to an appropriate vessel equipped with a stirrer and a heating source. The wax (if utilized) and solvent are charged thereto and agitated until homogeneous. After a homogeneous solution has been obtained, the mixture is heated to above 30° C., and preferably to above 65° C., while maintaining agitation. The magnesium oxide and/or calcium oxide is charged thereto over a period of 10 to 60 minutes while the temperature is increased to above 75° C., and preferably to above 85° C. During the addition of the magnesium oxide or calcium oxide or mixtures thereof, high agitation is employed in order to intimately mix the constituents to insure reaction. After all the magnesium oxide or calcium oxide has been added, the admixture is agitated for 30 minutes to 4 hours at 85° to 110° C. After the reaction is complete, as is determined by visible homogeneity and lack of particulates therein, it may be further diluted with a solvent and wax may be added and the reaction mixture cooled to room temperature and poured into appropriate vessels for further use.

It is to be noted under this first procedure that the water of addition is to be closely controlled so as to add the appropriate amount of water in order to have sufficient reactivity of the magnesium or calcium oxide, but care must be taken that additional water is not introduced into the reaction mixture to above the limits hereinbefore set forth which will reduce the corrosion resistance of compositions produced therefrom.

The second reaction procedure involves the use of excess water with subsequent removal by azeotropic distillation. In the second reaction procedure, to an appropriate vessel equipped with a stirrer, thermometer, reflux condenser and Dean and Stark trap and a heating mantel are charged, the organic sulfonic acid, wax (if utilized) and solvent. The mixture is agitated until a homogeneous solution is obtained and then the water is introduced thereto. The water in this instance is a molar ratio above that which has been previously specified (i.e. a 1 to 5 fold molar excess of water). The reaction mixture is heated to 66° C. the magnesium and/or calcium oxide is added thereto over 10 to 60 minutes. After all of the oxide has been added, the reaction mixture is heated to reflux, with agitation, and excess water is azeotropically removed therefrom and collected in the Dean and Stark trap. After the water distillation has ceased, the reaction is stopped and the reaction mixture cooled with stirring to 40° C. and poured from the flask.

The reaction procedure is the same as outlined above when organic carboxylic acids are utilized, forming a portion of the acid in the reaction as a substitute for the organic sulfonic acid. Additional wax and solvent may be added to form coating compositions in accordance with the invention. For a coating composition having excellent salt spray resistance, such composition should contain between 10 and 50 percent wax, and more preferably up to about 35 percent wax. Additional solvent may be added to obtain the desired viscosity. When the composition is coated, the volatile organic solvent evaporates therefrom and a flexible coating results. These compositions are useful in coating steel, aluminum, copper and other corrodible metals. The coatings may be applied as undercoats for automobiles, trucks, tractors and the like, and similar applications well recognized by those skilled in the art. The following examples will more fully illustrate the invention.

EXAMPLE 1

To a reaction vessel were charged 140 grams (0.2 mole) of alkylbenzene sulfonic acid solution. The solution was 70 percent alkylbenzene sulfonic acid dissolved in an organic solvent. The molecular weight of the neat alkylbenzene sulfonic acid was 500 grams per equivalent, and 714 grams per equivalent for the alkylbenzene sulfonic acid solution. To the alkylbenzene sulfonic acid were added 57 grams of distillate wax having a melting point of 150° F., along with 50.4 grams of water and 100 grams of mineral spirits having a boiling point of 300° to 410° F. The mixture was heated to 65° C., with agitation, and 80 grams of calcium oxide and 80 grams of magnesium oxide, which were preblended, were added thereto over a period of about 30 minutes. After addition of the basic oxides, the temperature was increased to 90° C. with vigorous agitation. After complete reaction was determined by the absence of particulates therein, 154 grams of mineral spirits were added thereto and the reaction mixture cooled to 40° C. The reaction product was a light tan thixotropic gel having a Brookfield viscosity of 15,000 cps. at 77° F.

A coating composition was prepared by blending 60 parts by weight of the reaction product, 20 parts by weight of the wax previously described, and 20 parts by weight of mineral spirits. The coating composition and the neat reaction product were coated on polished steel panels to impart a dried coating thickness of 1 to 2 mils. The coatings were dried and aged for 72 hours and then placed in a salt spray cabinet and run at 94° F. with a 5 percent salt fog. The coating composition failed after 480 salt spray hours and the neat reaction mixture failed after 144 salt spray hours.

EXAMPLE 2

Example 1 was repeated, except that 4 moles of magnesium oxide and 0.4 mole of water were utilized, rendering a molar ratio of 0.1:1 water to magnesium oxide. The reaction product failed after 24 salt spray hours.

EXAMPLE 3

Example 2 was repeated, except that the mole ratio of water to magnesium oxide was 0.7:1. The reaction product failed after 16 salt spray hours.

EXAMPLE 4

Example 1 was repeated, except that the water to magnesium oxide/calcium oxide was 1.6:1. The reaction product failed after 16 salt spray hours.

EXAMPLE 5

Example 2 was repeated, except that the water to magnesium oxide ratio was 1.2:1. The reaction product failed after 16 salt spray hours.

EXAMPLE 6

To a 1 liter 3-neck flask equipped with a stirrer, thermometer, reflux condenser, Dean and Stark trap, and a heating mantel were charged 140 grams (0.2 mole) of the sulfonic acid solution of Example 1, 57 grams of the wax and 273 grams of mineral spirits. One hundred grams (5.6 moles) of water were added slowly, with stirring, and the mixture was heated to 65° C. While at 65° C., 224 grams (4 moles) of calcium oxide were added over 60 minutes. After all the oxide had been added, the reaction mixture was heated to reflux and the water was azeotropically removed therefrom. After the water distillation ceased, the reaction was complete and the reaction product was cooled. The final water to oxide ratio was 0.7:1. A coating composition was prepared as previously described using 60 parts by weight of the reaction product, 20 parts by weight wax and 20 parts by weight mineral spirits. The reaction product had a Brookfield viscosity of 13,000 cps. at 77° F., and the coating composition had a Brookfield viscosity of 18,000 cps. at 77° F. The reaction product and the coating composition were coated on panels in accordance with Example 1. These coatings failed at about 1560 salt spray hours.

EXAMPLES 7-8

Example 6 was repeated, except that 23 grams (0.02 mole based on free acid) of oxidized petrolatum carboxylic acid were substituted for 0.02 mole of the alkylbenzene sulfonic acid, and magnesium oxide substituted for calcium oxide on a molar basis. In the first example herein, Example 7, the water to oxide ratio was 0.675:1, and in the second instance, Example 8, it was 0.53:1. Both reaction products had greater than 984 salt spray hours, and the coatings prepared therewith in Example 7 had 288 salt spray hours, and in Example 8 had 1128 salt spray hours.

Example 7 was repeated, except that the water to oxide ratio was 0.75:1. The resulting reaction product failed after 24 salt spray hours.

Thus, in accordance with the present invention, reaction products and coating compositions prepared therefrom are obtained. These reaction products and compositions are based upon magnesium oxide and calcium oxide having water to oxide molar ratios of less than 0.7:1 in the case of major amounts of magnesium oxide constituents, and water ratios of 2.5:1 in cases of major amounts of calcium oxide.

Although the invention has been described with specific reference to specific materials, it is only to be limited so far as is set forth in the accompanying claims.

I claim:

1. A noncarbonated complex comprising the reaction product of:
   (a) a basic oxide selected from the group consisting of calcium and magnesium oxide and mixtures thereof;
   (b) an organic sulfonic acid having an equivalent weight of about 300 to 750 grams per equivalent; and
   (c) water;
   wherein the molar ratio of basic oxide to organic sulfonic acid is at least 10:1; the molar ratio of water to basic oxide is less than 2.5:1 and greater than 0.5:1 when the basic oxide is at least 30 percent calcium oxide; and the molar ratio of water to basic oxide is less than 0.7:1 and greater than 0.3:1 when the basic oxide comprises substantially magnesium oxide and less than 30 percent calcium oxide.

2. The complex of claim 1 wherein the basic oxide consists of calcium oxide.

3. The complex of claim 2 wherein the molar ratio of water to calcium oxide is at or below 1.4:1.

4. The complex of claim 1 wherein the molar ratio of the basic oxide to organic sulfonic acid is 15-20:1.

5. The complex of claim 1 including an organic carboxylic acid.

6. The complex of claim 5 wherein the organic carboxylic acid is oxidized petrolatum.

7. The complex of claim 5 wherein the organic carboxylic acid is present at a level of up to 50 molar percent of the acid content of the complex.

8. A coating composition comprised of the complex of claim 1 and a wax.

9. The coating composition of claim 8 wherein said wax is present at a level of 10 to 50 percent by weight.

10. The complex of claim 2 including an organic carboxylic acid.

11. The complex of claim 10 wherein said organic carboxylic acid is oxidized petrolatum.

12. A coating composition comprised of the reaction product of claim 10 and wax.

* * * * *

UNITED STATES PATENT AND TRADEMARK OFFICE
CERTIFICATE OF CORRECTION

PATENT NO. : 4,475,949

DATED : October 9, 1984

INVENTOR(S) : Norman C. Ross et al.

It is certified that error appears in the above-identified patent and that said Letters Patent is hereby corrected as shown below:

Column 2 Line 28 After "wax" insert --sulfonic--.

Column 4 Line 36 After "66°C." insert

--under agitation and at 65°C--.

Signed and Sealed this

Twelfth Day of March 1985

[SEAL]

Attest:

DONALD J. QUIGG

*Attesting Officer*     Acting Commissioner of Patents and Trademarks